(12) United States Patent
Sakurai

(10) Patent No.: US 9,019,611 B2
(45) Date of Patent: Apr. 28, 2015

(54) OPTICAL MODULE AND ELECTRONIC APPARATUS

(71) Applicant: Seiko Epson Corporation, Tokyo (JP)

(72) Inventor: Kazunori Sakurai, Chino (JP)

(73) Assignee: Seiko Epson Corporation (JP)

( * ) Notice: Subject to any disclaimer, the term of this patent is extended or adjusted under 35 U.S.C. 154(b) by 0 days.

(21) Appl. No.: 14/260,759

(22) Filed: Apr. 24, 2014

(65) Prior Publication Data

US 2014/0233103 A1    Aug. 21, 2014

Related U.S. Application Data

(63) Continuation of application No. 13/398,149, filed on Feb. 16, 2012, now Pat. No. 8,743,461.

(30) Foreign Application Priority Data

Feb. 17, 2011  (JP) ................................. 2011-032432

(51) Int. Cl.
| | |
|---|---|
| *G02B 27/00* | (2006.01) |
| *G02B 5/28* | (2006.01) |
| *G01J 3/50* | (2006.01) |
| *G01J 3/51* | (2006.01) |
| *G02B 26/00* | (2006.01) |
| *G01N 21/3504* | (2014.01) |
| *G01N 21/25* | (2006.01) |
| *G01N 21/552* | (2014.01) |

(Continued)

(52) U.S. Cl.
CPC ... *G02B 5/28* (2013.01); *G01J 3/50* (2013.01); *G01J 3/51* (2013.01); *G02B 26/001* (2013.01); *G01N 21/3504* (2013.01); *G01N 21/251* (2013.01); *G01N 21/255* (2013.01); *G01N 21/554* (2013.01); *G01N 21/658* (2013.01); *G01J 2003/1226* (2013.01)

(58) Field of Classification Search
CPC ...... G02B 27/646; G02B 26/001; G02B 5/28; G02B 26/007; G02B 26/06; G02B 26/0841
USPC .................. 359/557, 578, 579, 260, 261, 263
See application file for complete search history.

(56) References Cited

U.S. PATENT DOCUMENTS

| 4,744,619 A | 5/1988 | Cameron |
|---|---|---|
| 5,526,452 A | 6/1996 | Dannoux et al. |
| 5,838,405 A | 11/1998 | Izumi et al. |

(Continued)

FOREIGN PATENT DOCUMENTS

| JP | 61-502706 | 11/1986 |
|---|---|---|
| JP | 06-196747 | 7/1994 |

(Continued)

*Primary Examiner* — Thomas K Pham
*Assistant Examiner* — Sharrief Broome
(74) *Attorney, Agent, or Firm* — Harness, Dickey & Pierce, P.L.C.

(57) ABSTRACT

An optical module (colorimetry sensor) includes an interference filter, and a transparent substrate to which a first substrate of the interference filter is fixed, having a second thermal expansion coefficient which has a value different from a first thermal expansion coefficient. The interference filter is fixed to the transparent substrate through an adhesive layer made of gel-like resin, and the adhesive layer alleviates stress generated due to a difference in the thermal expansion coefficients between the interference filter and the transparent substrate.

10 Claims, 10 Drawing Sheets

(51) Int. Cl.
*G01N 21/65* (2006.01)
*G01J 3/12* (2006.01)

(56) References Cited

U.S. PATENT DOCUMENTS

| | | | |
|---|---|---|---|
| 6,266,472 | B1 | 7/2001 | Norwood et al. |
| 6,298,027 | B1 | 10/2001 | Wilde et al. |
| 6,324,319 | B1 | 11/2001 | Tselikov et al. |
| 6,443,632 | B2 | 9/2002 | Ando et al. |
| 6,461,059 | B2 | 10/2002 | Ando et al. |
| 6,529,464 | B2 | 3/2003 | Wilde et al. |
| 6,538,974 | B2 | 3/2003 | Wilde et al. |
| 6,587,421 | B1 | 7/2003 | Wilde et al. |
| 6,609,841 | B1 | 8/2003 | Wilde et al. |
| 7,065,106 | B2 | 6/2006 | Aronson |
| 7,174,062 | B2 | 2/2007 | Fukuyama et al. |
| 7,195,402 | B2 | 3/2007 | Fukuyama et al. |
| 7,308,174 | B2 | 12/2007 | Fukuyama et al. |
| 7,321,703 | B2 | 1/2008 | Fukuyama et al. |
| 7,325,982 | B2 | 2/2008 | Aronson |
| 7,428,351 | B2 | 9/2008 | Jenkins et al. |
| 7,539,370 | B2 | 5/2009 | Yamazaki |
| 7,697,022 | B2 | 4/2010 | Gomi |
| 2004/0066809 | A1 | 4/2004 | Oguri et al. |
| 2005/0089262 | A1 | 4/2005 | Jenkins et al. |
| 2007/0228552 | A1 | 10/2007 | Takeuchi et al. |
| 2008/0291541 | A1 | 11/2008 | Padiyath et al. |
| 2011/0305415 | A1 | 12/2011 | Kawai |

FOREIGN PATENT DOCUMENTS

| | | | |
|---|---|---|---|
| JP | 07-181343 | | 7/1995 |
| JP | 08-271871 | | 10/1996 |
| JP | 09-101431 | | 4/1997 |
| JP | 10-084105 | | 3/1998 |
| JP | 11-317837 | | 11/1999 |
| JP | 2000-131583 | A | 5/2000 |
| JP | 2001-281505 | A | 10/2001 |
| JP | 2002-176157 | A | 6/2002 |
| JP | 2002-243546 | A | 8/2002 |
| JP | 2003-508815 | A | 3/2003 |
| JP | 2003-510628 | A | 3/2003 |
| JP | 2003-522362 | A | 7/2003 |
| JP | 2003-532963 | A | 11/2003 |
| JP | 2005-516253 | A | 6/2005 |
| JP | 2007-525722 | A | 9/2007 |
| JP | 2007-266260 | A | 10/2007 |
| JP | 2008-080759 | A | 4/2008 |
| JP | 2008-224941 | A | 9/2008 |
| JP | 2009-016594 | A | 1/2009 |
| JP | 2009-099379 | A | 5/2009 |
| JP | 2009-134027 | A * | 6/2009 |
| JP | 2009-134027 | A | 6/2009 |
| JP | 2010-527815 | A | 8/2010 |
| JP | 2010-217236 | A | 9/2010 |
| JP | 2010-224513 | A | 10/2010 |
| WO | WO-01/22128 | A1 | 3/2001 |
| WO | WO-2004-057396 | A1 | 7/2004 |

* cited by examiner

OPTICAL MODULE AND ELECTRONIC APPARATUS

CROSS-REFERENCE TO RELATED APPLICATIONS

This is a continuation patent application of U.S. application Ser. No. 13/398,149 filed Feb. 16, 2012, which claims priority to Japanese Patent Application No. 2011-032432, filed Feb. 17, 2011, all of which are expressly incorporated by reference herein in their entireties.

BACKGROUND

1. Technical Field

The present invention relates to an optical module and an electronic apparatus which include an interference filter which separates light of a predetermined wavelength from incident light.

2. Related Art

In the related art, an interference filter has been proposed which transmits or reflects only light of a predetermined wavelength from incident light (refer to JP-A-2009-134027, for example).

JP-A-2009-134027 discloses an optical device (interference filter) in which a pair of substrates face each other and reflection films are respectively formed on the surfaces of the substrates which face each other. In such an interference filter, a gap is formed between the pair of reflection films, and the dimension of the gap determines the wavelength of light which can be separated. Thus, in such an interference filter, it is necessary to maintain the pair of reflection films parallel to each other in order to separate light of a predetermined wavelength with high accuracy.

In this regard, the interference filter is fixed to a transparent substrate, a light receiving element or the like by an adhesive agent and is used as an optical module. However, in a case where the optical module is used in an environment having a large temperature change, stress is generated due to a difference in the thermal expansion coefficients between the transparent substrate, the light receiving element or the like and the interference filter, which causes distortion in the interference filter. As a result, a problem arises such that the gap between the reflection films becomes uneven, and thus, deviation occurs in the separated wavelength or the half-value width is changed.

SUMMARY

An advantage of some aspects of the invention is to provide an optical module and an electronic apparatus which include an interference filter with high spectral accuracy even in a case where the interference filter is used in an environment having a large temperature change.

An aspect of the invention is directed to an optical module including: an interference filter including a first substrate having a first thermal expansion coefficient, a second substrate which faces the first substrate, a first reflection film which is formed on the first substrate, and a second reflection film which is formed on the second substrate and faces the first reflection film through a gap; and a fixing portion to which the first substrate of the interference filter is fixed, having a second thermal expansion coefficient which has a value different from the first thermal expansion coefficient, wherein the interference filter is fixed to the fixing portion through an adhesive layer of gel-like resin.

In an optical module in the related art, in a case where the optical module is used in an environment having a large temperature change, there is a problem caused by stress generated due to a difference in the thermal expansion coefficients between a fixing portion such as a transparent substrate or a light receiving element and an interference filter. That is, since the fixing portion and the interference filter are different from each other in displacement due to thermal expansion, shear stress is applied to an adhesive layer disposed between the fixing portion and the interference filter. Further, since a force corresponding to the shear stress is also applied to the interference filter, distortion occurs in the interference filter.

On the other hand, according to this aspect of the invention, even though stress is generated due to the difference in the thermal expansion coefficients between the fixing portion and the interference filter, it is possible to alleviate the stress through the adhesive layer made of the gel-like resin which is disposed between the fixing portion and the interference filter. Accordingly, it is possible to sufficiently suppress occurrence of distortion of the interference filter. Thus, it is possible to maintain high spectral accuracy even in a case where the optical module is used in an environment having a large temperature change.

In the optical module according to this aspect, it is preferable that, when the thickness of the adhesive layer is Ta (mm), the linear expansion coefficient of the first substrate is $\alpha 1$ ($K^{-1}$), the Young's modulus of the first substrate is E1 (GPa), the thickness of the first substrate is T1 (mm), the linear expansion coefficient of the fixing portion is $\alpha 2$ ($K^{-1}$), the Young's modulus of the fixing portion is E2 (GPa), the thickness of the fixing portion is T2 (mm), and a coefficient based on the gel-like resin is A, the thickness of the adhesive layer satisfies the following formula (1) in a case where $(\alpha 1 \cdot E1 \cdot T1^2) \leq (\alpha 2 \cdot E2 \cdot T2^2)$, and satisfies the following formula (2) in a case where $(\alpha 1 \cdot E1 \cdot T1^2) > (\alpha 2 \cdot E2 \cdot T2^2)$.

$$Ta \geq A \cdot (\alpha 2 \cdot E2 \cdot T2^2)/(\alpha 1 \cdot E1 \cdot T1^2) \quad (1)$$

$$Ta \geq A \cdot (\alpha 1 \cdot E1 \cdot T1^2)/(\alpha 2 \cdot E2 \cdot T2^2) \quad (2)$$

In this configuration, the thickness of the adhesive layer satisfies the above conditions. In this way, in a case where the thickness of the adhesive layer satisfies the above conditions, it is possible to sufficiently alleviate the shear stress applied to the adhesive layer. Thus, it is possible to reliably alleviate the stress generated due to the difference in the thermal expansion coefficients between the fixing portion and the interference filter.

In the optical module according to this aspect, it is preferable that the Young's modulus of the adhesive layer is 10 kPa or more and 100 kPa or less.

Here, in a case where the Young's modulus of the adhesive layer is less than 10 kPa, flowability of the adhesive layer becomes large, and thus, the position of the interference filter with respect to the fixing portion due to vibration applied to the optical module is deviated, for example. On the other hand, in a case where the Young's modulus of the adhesive layer is larger than 100 kPa, for example, when surrounding temperature is changed, it is difficult to sufficiently suppress the stress generated due to the difference in the thermal expansion coefficients between the fixing portion and the interference filter, which may cause warping in the interference filter.

On the other hand, as described above, in a case where the Young's modulus of the adhesive layer is 10 kPa or more and 100 kPa or less, it is possible to sufficiently alleviate the shear stress applied to the adhesive layer, and to prevent deviation of the position of the interference filter with respect to the fixing portion.

In the optical module according to this aspect, it is preferable that the interference filter includes a light transmission region which transmits light multiple-interfered by the first reflection film and the second reflection film, and the adhesive layer can transmit the light, has a refraction index which is close to that of the first substrate compared with air, and is disposed in a region which overlaps with the light transmission region from a plan view when the first substrate and the second substrate are seen in a substrate thickness direction.

In this configuration, the adhesive layer is disposed in the region which overlaps with the light transmission region from a plan view. In this case, the light which is incident on the interference filter reaches the fixing portion through the adhesive layer. Further, since the adhesive layer has the refraction index which is close to that of the first substrate compared with air, loss of the incident light becomes small in a case where the incident light passes through the adhesive layer. Thus, according to this configuration, it is possible to reduce loss of the incident light due to reflection.

In the optical module according to this aspect, it is preferable that the first substrate and the second substrate are glass substrates, and the refraction index of the adhesive layer is 1.3 or more and 1.7 or less.

In a case where the refraction index of the adhesive layer is within the above-mentioned range, if the first substrate and the fixing portion are made of normal materials, it is possible to reduce the difference between the refraction index of the first substrate or the fixing portion and the refraction index of the adhesive layer. Thus, according to this configuration, it is possible to reduce loss of the incident light due to reflection.

In the optical module according to this aspect, it is preferable that a part of the interference filter is fixed to the fixing portion through a cured adhesive layer obtained by curing a curable adhesive agent, and the other part of the interference filter is fixed to the fixing portion through the adhesive layer.

In this configuration, a part of the interference filter is fixed to the fixing portion through the cured adhesive layer obtained by curing the curable adhesive agent. In a case where such a cured adhesive agent is used, it is possible to reliably fix the interference filter to the fixing portion, compared with a case where the gel-like resin is used. Thus, it is possible to suppress deviation of the position of the interference filter.

On the other hand, since the other part of the interference filter is fixed to the fixing portion through the adhesive layer, as described above, it is possible to sufficiently suppress occurrence of distortion of the interference filter. In this way, it is possible to enhance the adhesive strength between the interference filter and the fixing portion.

Here, it is preferable that a part of the interference filter is present in one location. In a case where a plurality of locations are fixed by the cured adhesive layer, the effect of sufficiently suppressing occurrence of distortion of the interference filter tends to become weak.

In the optical module according to this aspect, it is preferable that the Young's modulus of the cured adhesive layer is 1 MPa or more.

In this way, in a case where the Young's modulus of the cured adhesive layer is 1 MPa or more, it is possible to reliably fix the interference filter to the fixing portion compared with a case where the gel-like resin is used. Thus, according to this configuration, it is possible to enhance the adhesive strength between the interference filter and the fixing portion. Further, it is possible to suppress deviation of the position of the interference filter.

In the optical module according to this aspect, it is preferable that the interference filter includes an electrode terminal which is disposed on the first substrate, and the cured adhesive layer is disposed in a part of a region which overlaps with the electrode terminal from a plan view when the first substrate and the second substrate are seen in a substrate thickness direction.

In this configuration, the cured adhesive layer is disposed in the region which overlaps with the electrode terminal from a plan view. In the part of the interference filter on which the electrode terminal is disposed, even though distortion occurs, the distortion does not significantly affect the spectral accuracy of the interference filter. In this way, it is possible to enhance the adhesive strength between the interference filter and the fixing portion while sufficiently maintaining the spectral accuracy. Further, even though external stress is applied when a wiring is installed to the electrode terminal, it is possible to suppress a problem such as position deviation, inclination or the like of the interference filter.

In the optical module according to this aspect, it is preferable that the fixing portion is a transparent substrate which is capable of transmitting light which passes through the interference filter.

In this configuration, the interference filter is fixed to the transparent substrate through the adhesive layer. Thus, if a light receiving element is disposed so that light which passes through the interference filter and the transparent substrate is incident on the light receiving element, it is possible to obtain a desired optical module.

In the optical module according to this aspect, it is preferable that the fixing portion is a light receiving element which receives light which passes through the interference filter.

In this configuration, since the interference filter is fixed to the light receiving element through the adhesive layer, it is possible to obtain a desired optical module as it is.

It is preferable that the optical module according to this aspect further includes a casing which includes an exterior portion, a light incident substrate through which light incident on the interference filter is introduced and a light exiting substrate through which light passing through the interference filter exits, and is formed therein with a hermetically sealed space, and the interference filter is accommodated in the casing.

In this configuration, the interference filter is accommodated in the casing. Thus, for example, by filling an inert gas in the casing or by decompressing the inside of the casing, it is possible to suppress electric power use in the interference filter, and to suppress deterioration of the interference filter due to oxidation or the like.

Further, in this configuration, since the casing includes the light incident substrate and the light exiting substrate, if the light receiving element is disposed so that light which passes through the casing is incident on the light receiving element, it is possible to obtain a desired optical module.

In the optical module according to this aspect, it is preferable that the fixing portion is the light exiting substrate of the casing.

According to this configuration, by accommodating the interference filter in the casing in this way, it is possible to suppress electric power use in the interference filter, and to suppress deterioration of the interference filter due to oxidation or the like.

Another aspect of the invention is directed to an electronic apparatus including the above-described optical module.

Here, as the electronic apparatus, an optical measurement apparatus which analyzes chromaticity, brightness or the like of light which is incident on the optical module on the basis of an electric signal which is output from the optical module, a gas detection apparatus which detects an absorption wavelength of gas to inspect the kind of the gas, an optical communication apparatus which acquires data included in wavelength of light from received light, or the like may be used, for example.

In this configuration, as described above, the electronic apparatus includes the optical module. As described above, since the optical module has high spectral accuracy, it is possible to obtain a detection result with high accuracy. Thus, in the electronic apparatus including such an optical module, it is possible to perform an optical analysis process with accuracy, on the basis of the detection result of high accuracy.

BRIEF DESCRIPTION OF THE DRAWINGS

The invention will be described with reference to the accompanying drawings, wherein like numbers reference like elements.

DESCRIPTION OF EXEMPLARY EMBODIMENTS

First Embodiment

Hereinafter, a first embodiment of the invention will be described with reference to the accompanying drawings.

1. Overall Configuration of Optical Device

Figure 1:
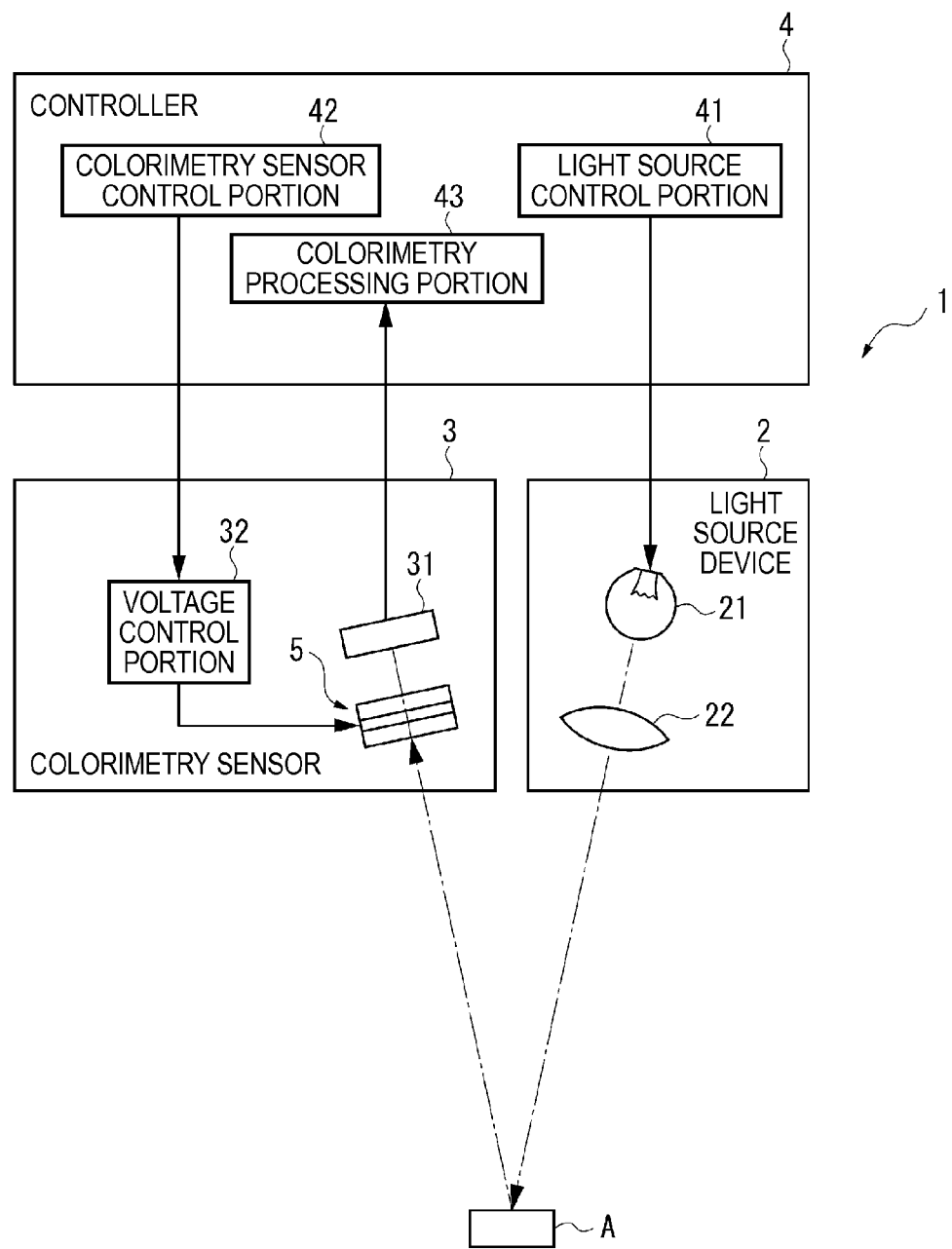
FIG. 1 is a diagram schematically illustrating a configuration of a colorimeter (electronic apparatus) of a first embodiment according to the invention.

FIG. 1 is a diagram schematically illustrating a configuration of a colorimeter (electronic apparatus) according to an embodiment of the invention.

A colorimeter 1 is an electronic apparatus according to the invention, and as shown in FIG. 1, includes a light source device 2 which emits light to a measurement target A, a colorimetry sensor 3 which is an optical module according to the invention, and a controller 4 which controls an overall operation of the colorimeter 1. Further, as the measurement target A reflects light emitted from the light source device 2 and the colorimetry sensor 3 receives the reflected light to be inspected, the colorimeter 1 analyzes and measures the chromaticity of the light to be inspected, that is, the color of the measurement target A on the basis of a detection signal output from the colorimetry sensor 3.

2. Configuration of Light Source Device

The light source device 2 includes a light source 21 and a plurality of lenses 22 (only one lens is shown in FIG. 1), and emits white light to the measurement target A. The plurality of lenses 22 may include a collimator lens. In this case, in the light source device 2, the white light emitted from the light source 21 is collimated through the collimator lens, and the collimated light exits through a projection lens (not shown) toward the measurement target A.

In the present embodiment, the colorimeter 1 including the light source device 2 is described as an example, but in a case where the measurement target A is a light emitting member, a configuration in which the light source device 2 is not provided may be used.

3. Configuration of Colorimetry Sensor

The colorimetry sensor 3 forms a light module according to the invention. As shown in FIG. 1, the colorimetry sensor 3 includes an interference filter 5, a light receiving device 31 which receives and detects the light passed through the interference filter 5, and a voltage control portion 32 which applies a drive voltage to the interference filter 5. Further, the colorimetry sensor 3 includes a light incident optical lens (not shown) which guides the light reflected by the measurement target A (light to be inspected) to a position which faces the interference filter 5 to the inside thereof. The colorimetry sensor 3 separates only light of a predetermined wavelength from the light to be inspected which is incident through the light incident optical lens by the interference filter 5, and receives the separated light by the light receiving device 31.

The light receiving device 31 includes a plurality of photoelectric conversion elements and generates an electric signal according to the amount of received light. Further, the light receiving device 31 is connected to the controller 4 and outputs the generated electric signal to the controller 4 as a received light signal.

In the colorimetry sensor 3, as described later, the interference filter 5 is fixed to a transparent substrate 7 through an adhesive layer 6 made of gel-like resin.

3-1. Configuration of Interference Filter

Figure 2:
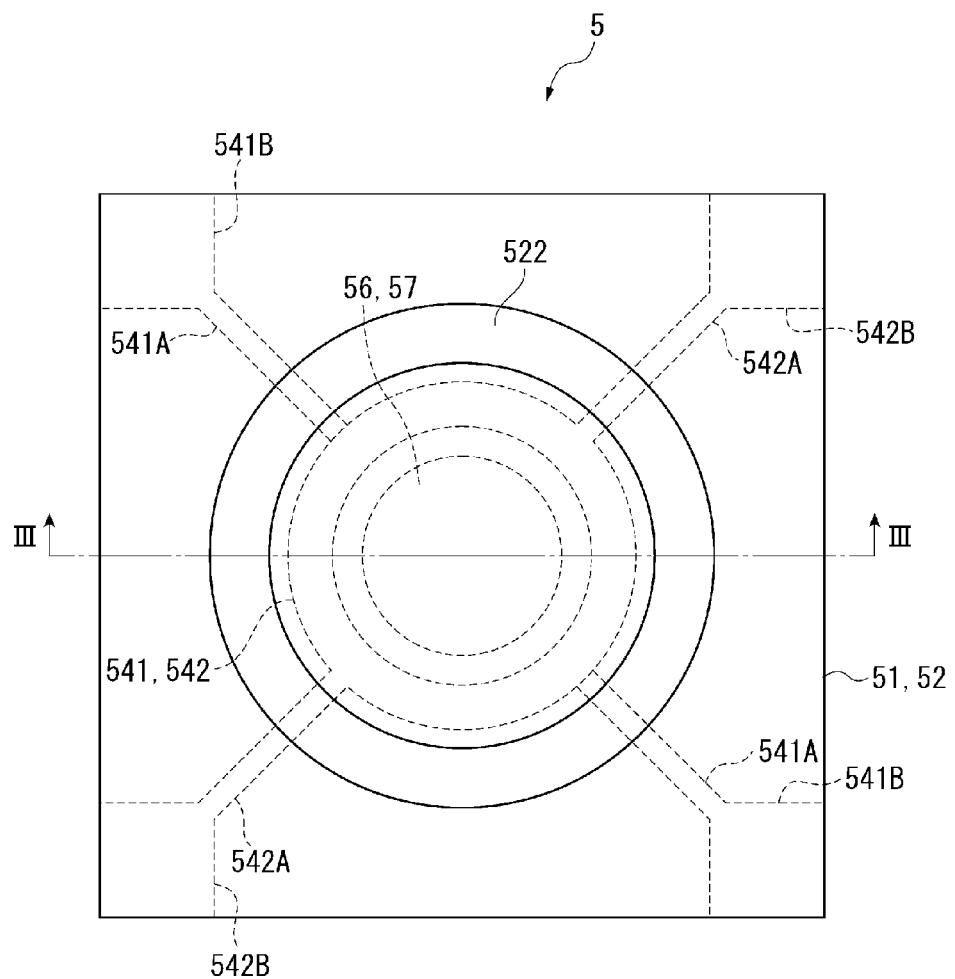
FIG. 2 is a plan view schematically illustrating a configuration of an interference filter according to the first embodiment.
Figure 3:
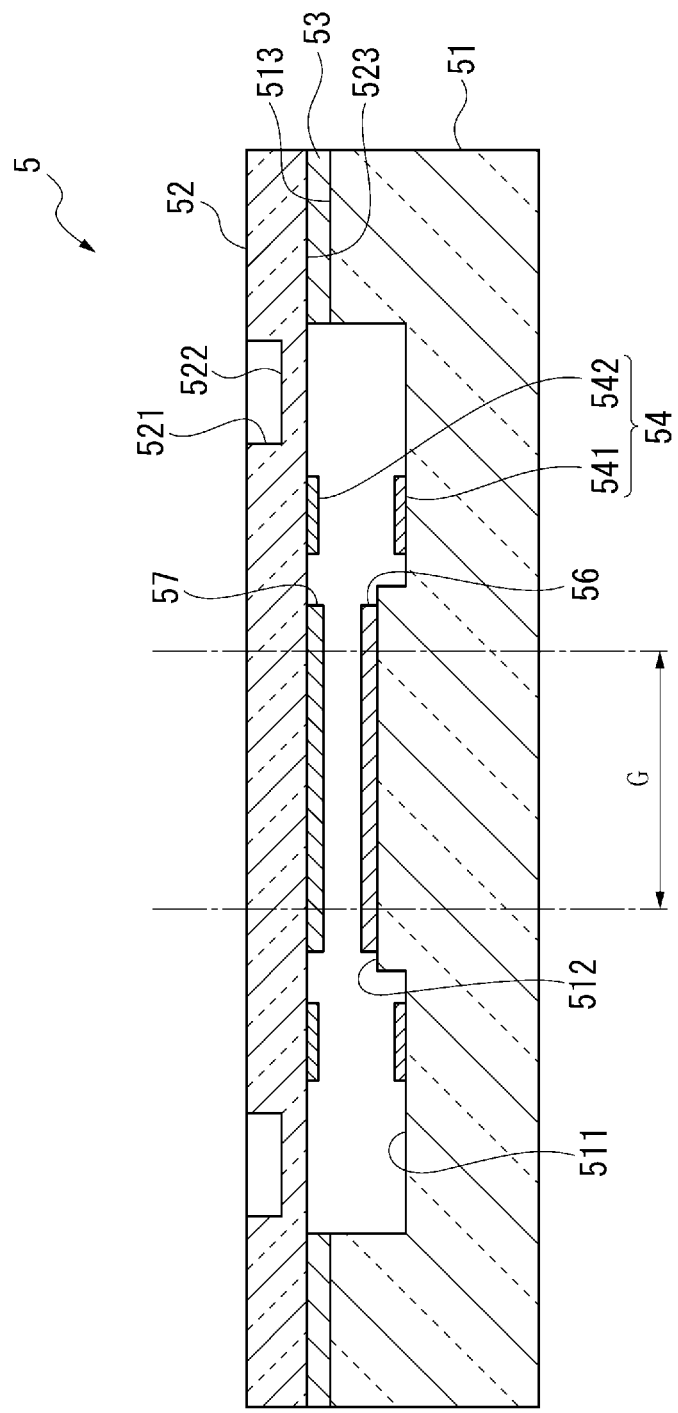
FIG. 3 is a cross-sectional view illustrating an interference filter taken along line III-III in FIG. 2.

FIG. 2 is a plan view illustrating the interference filter 5 when seen from a plan view in the substrate thickness direction. FIG. 3 is a cross-sectional view of the interference filter 5 taken along line III-III in FIG. 2.

As shown in FIG. 2, the interference filter 5 includes a first substrate 51 and a second substrate 52. The two substrates 51 and 52 are respectively made of a variety of glasses such as soda glass, crystalline glass, quartz glass, lead glass, potassium glass, borosilicate glass or non-alkali glass, or a material such as crystal capable of transmitting light in a visible light range. Further, as shown in FIG. 3, the two substrates 51 and 52 are integrally formed by bonding surfaces 513 and 523 which are formed along an outer peripheral edge by a plasma polymer film 53 in which siloxane is a main component, for example.

Further, a first reflection film. 56 and a second reflection film 57 are formed between the first substrate 51 and the second substrate 52. Here, the first reflection film 56 is fixed to the surface of the first substrate 51 which faces the second substrate 52, and the second reflection film 57 is fixed to the surface of the second substrate 52 which faces the first substrate 51. Further, the first reflection film 56 and the second reflection film 57 face each other through a gap. Here, a space narrowed by the first reflection film 56 and the second reflection film. 57 is referred to as a light transmission region G. Further, the interference filter 5 allows the incident light to be multiple-interfered in the light transmission region G, and transmits the reinforced light.

Further, an electrostatic actuator 54 which is a gap movable portion of the invention for adjustment of the size of the gap is provided between the first substrate 51 and the second substrate 52. The electrostatic actuator 54 includes a first electrode 541 disposed in the first substrate 51 and a second electrode 542 disposed in the second substrate 52.

3-1-1. Configuration of First Substrate

The first substrate 51 has an electrode groove 511 and a mirror fixing portion 512 formed on the surface thereof which faces the second substrate 52 by etching.

Although not shown, the electrode groove 511 is formed in a ring shape centering around a plane central point of the first substrate 51 in the plan view of the filter seen in the substrate thickness direction.

The mirror fixing portion 512 is formed in a cylindrical shape which protrudes toward the second substrate 52 on the same axis as the electrode groove 511.

On the bottom of the groove of the electrode groove 511, the first electrode 541 of a ring shape which forms the electrostatic actuator 54 is formed. Further, the first electrode 541 has a first electrode line 541A which extends along a wiring groove toward an outer peripheral portion of the first substrate 51. Further, a first electrode terminal 541B which is a tip end of the first electrode line 541A is connected to the voltage control portion 32.

Further, the first reflection film 56 is fixed to the surface of the mirror fixing portion 512 which faces the second substrate 52. The first reflection film 56 may be a dielectric multilayer reflection film obtained by layering $TiO_2$ and $SiO_2$, for example, and may be a metal film such as an Ag alloy. Further, both of the dielectric multilayer reflection film and the metal film may be layered.

Further, the first bonding surface 513 is formed outside the electrode groove 511 of the first substrate 51. As described above, the plasma polymer film 53 which bonds the first substrate 51 and the second substrate 52 is formed on the first bonding surface 513.

3-1-2. Configuration of Second Substrate

The second substrate 52 is formed by processing the surface which does not face the first substrate 51 by etching. The second substrate 52 includes a cylindrical movable portion 521 centering around the substrate central point, and a holding portion 522 which is coaxial with the movable portion 521 and holds the movable portion 521. Here, the outer peripheral diameter of the holding portion 522 is formed to have the size which is slightly smaller than the outer peripheral diameter of the electrode groove 511 of the first substrate 51. Further, the inner peripheral diameter of the holding portion 522 is formed to have the size which is slightly larger than the outer peripheral diameter of the ring-shaped first electrode 541 of the first substrate 51.

The movable portion 521 is formed to have the thickness larger than that of the holding portion 522 so as to prevent warping. The holding portion 522 is a diaphragm which surrounds the movable portion 521, and has a thickness of 50 μm, for example.

In the present embodiment, the diaphragm-shaped holding portion 522 is shown as an example, but a holding portion having a plurality of pairs of beam structures disposed in positions which are point-symmetrical around the center of the movable portion may be disposed.

The ring-shaped second electrode 542 which faces the first electrode 541 with a predetermined interval is formed on the surface of the holding portion 522 which faces the first substrate 51. Here, as described above, the electrostatic actuator 54 is formed by the second electrode 542 and the above-described first electrode 541.

Further, a second electrode line 542A is formed toward the outer peripheral portion of the second electrode 52 from a part of an outer peripheral edge of the second electrode 542, and a second electrode terminal 542B which is a tip end of the second electrode line 542A is connected to the voltage control portion 32.

The second reflection film 57 which faces the first reflection film 56 is formed on the surface of the first movable portion 521 which faces the first substrate 51, through a gap. Since the configuration of the second reflection film 57 is the same as that of the first reflection film 56, its description will be omitted.

3-2. Specific Type of Colorimetry Sensor

Figure 4:
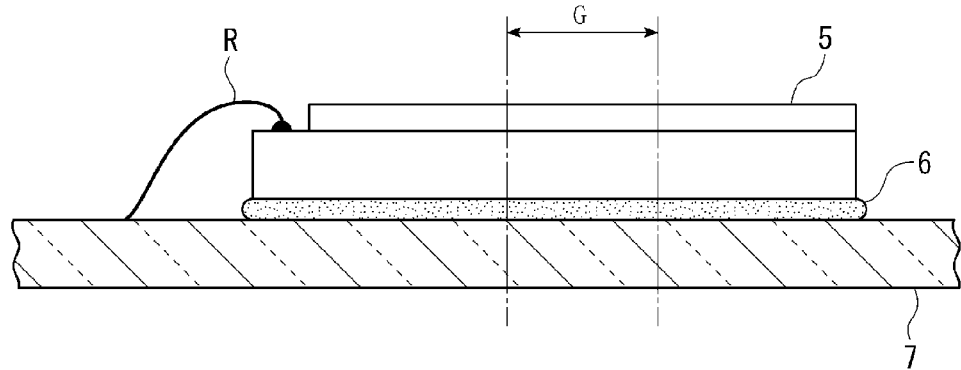
FIG. 4 is a cross-sectional view illustrating the vicinity of an interference filter in an optical module according to a first embodiment.

FIG. 4 is a cross-sectional view illustrating the vicinity of the interference filter 5 of the colorimetry sensor 3 (optical module) according to a first embodiment.

In the colorimetry sensor 3, as shown in FIG. 4, the above-described interference filter 5 is fixed to the transparent substrate 7 through the adhesive layer 6 formed of gel-like resin. Further, the interference filter 5 is connected to the voltage control portion 32 by a wiring R. Further, the adhesive layer 6 is formed in a region which overlaps with the light transmission region G when seen from a plan view. Here, the same material as the material of the first substrate 51 and the second substrate 52 may be used as material of the transparent substrate 7.

The adhesive layer 6 is a layer having physical properties which will be described later. Further, even though stress is generated due to a difference in the thermal expansion coefficients between the transparent substrate 7 and the interference filter 5, it is possible to alleviate the stress through the adhesive layer 6 disposed between the transparent substrate 7 and the interference filter 5. Thus, it is possible to sufficiently suppress occurrence of distortion in the interference filter 5.

3-3. Configuration of Adhesive Layer

The adhesive layer 6 is a layer formed of gel-like resin. It is preferable that the gel-like resin be resin capable of transmitting light of the visible light range, considering that it is possible to dispose the adhesive layer 6 in the region which overlaps with the light transmission region G, when seen from a plan view. On the other hand, in a case where the gel-like resin is disposed in a region which does not overlap with the light transmission region G when seen from a plan view, resin which does not transmit the light of the visible light range may be used. Silicon-based resin, acrylic-based resin, epoxy-based resin, urethane-based resin or the like may be used as the gel-like resin.

It is preferable that the adhesive layer 6 have the physical properties which will be described later.

That is, the thickness Ta (mm) of the adhesive layer 6 is set on the basis of linear expansion coefficients, Young's moduli and thicknesses of the first substrate 51 and the transparent substrate 7.

Here, when the linear expansion coefficient of the first substrate 51 is α1 (K$^{-1}$), the Young's modulus thereof is E1 (GPa), the thickness thereof is T1 (mm), the linear expansion coefficient of the transparent substrate 7 is α2 (K$^{-1}$), the Young's modulus thereof is E2 (GPa), the thickness thereof is T2 (mm), and a coefficient based on the gel-like resin is A, it is preferable that the thickness Ta of the adhesive layer 6 satisfy the following formula (1) in a case where (α1·E1·T1$^2$) ≤(α2·E2·T2$^2$), and satisfy the following formula (2) in a case where (α1·E1·T1$^2$)>(α2·E2·T2$^2$).

$$Ta \geq A \cdot (\alpha 2 \cdot E2 \cdot T2^2)/(\alpha 1 \cdot E1 \cdot T1^2) \tag{1}$$

$$Ta \geq A \cdot (\alpha 1 \cdot E1 \cdot T1^2)/(\alpha 2 \cdot E2 \cdot T2^2) \tag{2}$$

In the formulas (1) and (2), A is a coefficient based on the gel-like resin and is a value determined by the material of the gel-like resin. Specifically, A may be calculated by the following formula (3) in a case where the Young's modulus of the adhesive layer 6 is E3 (GPa).

$$A = E3/0.01 \tag{3}$$

In this way, in a case where the condition represented by the following formula (1) is satisfied in the case of (α1·E1·T1$^2$) ≤(α2·E2·T2$^2$), or in a case where a condition represented by the following formula (2) is satisfied in the case of (α1·E1·T1$^2$)>(α2·E2·T2$^2$), even though stress is generated due to difference in the thermal expansion coefficients between the transparent substrate 7 and the interference filter 5, it is possible to sufficiently alleviate shear stress applied to the adhesive layer 6 through the adhesive layer 6.

The Young's modulus can be measured by appropriately selecting known Young's modulus measurement methods such as a film strain method, a push-in test method, a Brillouin scattering method, an ultrasonic microscope method, or a resonance oscillation method. Further, the thermal expansion coefficient can be measured by measuring the amount of thermal expansion of a measurement sample from difference in the amounts of thermal expansion between the measurement sample and a reference sample when temperature is increased at a specific speed, using TMA (Thermo Mechanical Analysis).

Further, it is preferable that the Young's modulus of the adhesive layer 6 be 10 kPa or more and 100 kPa or less. In a case where the Young's modulus is within the above range, even though stress is generated due to the difference in the thermal expansion coefficients between the transparent substrate 7 and the interference filter 5, it is possible to sufficiently alleviate shear stress applied to the adhesive layer 6 through the adhesive layer 6.

Further, it is preferable that the refraction index of the adhesive layer 6 be 1.3 or more and 1.7 or less. In a case where the refraction index of the adhesive layer 6 is within the above range, if the first substrate 51 and the transparent substrate 7 are made of normal materials, it is possible to further reduce the difference between the refraction index of the first substrate 51 or the transparent substrate 7 and the refraction index of the adhesive layer 6.

3-4. Configuration of Voltage Control Portion

The voltage control portion 32 controls voltage applied to the first electrode 541 and the second electrode 542 of the electrostatic actuator 54 under the control of the controller 4.

4. Configuration of Controller

The controller 4 controls an overall operation of the colorimeter 1.

As the controller 4, for example, a general-purpose personal computer, a personal digital assistant, or a colorimetry dedicated computer may be used.

Further, as shown in FIG. 1, the controller 4 includes a light source control portion 41, a colorimetry sensor control portion 42 and a colorimetry processing portion 43.

The light source control portion 41 is connected to the light source device 2. Further, the light source control portion 41 outputs a predetermined control signal to the light source device 2 on the basis of a setting input of a user, for example, and allows white light of a predetermined brightness to be emitted from the light source device 2.

The colorimetry sensor control portion 42 is connected to the colorimetry sensor 3. Further, the colorimetry sensor control portion 42 sets wavelength of the light received by the colorimetry sensor 3 on the basis of a setting input of the user, for example, and then outputs a control signal for detection of the amount of received light of the wavelength to the colorimetry sensor 3. Thus, the voltage control portion 32 of the colorimetry sensor 3 sets the voltage applied to the electrostatic actuator 54 so as to transmit only the wavelength of the light desired by the user, on the basis of the control signal.

The colorimetry processing section 43 analyzes the chromaticity of the measurement target A from the amount of received light detected by the light receiving device 31.

5. Effects in the Present Embodiment

As described above, in a case where the colorimetry sensor 3 according to the present embodiment is used in an environment having a large temperature change, even though stress is generated due to the difference in the thermal expansion coefficients between the transparent substrate 7 and the first substrate 51 of the interference filter 5, it is possible to alleviate the stress through the adhesive layer 6 formed of gel-like resin disposed between the transparent substrate 7 and the first substrate 51. Thus, it is possible to sufficiently suppress occurrence of distortion in the interference filter 5. Thus, it is possible to maintain high spectral accuracy even in a case where the interference filter is used in an environment having a large temperature change.

In the colorimetry sensor 3 according to the present embodiment, the adhesive layer 6 is disposed in the region which overlaps with the light transmission region G when seen from a plan view. In such a case, the incident light incident on the interference filter 5 reaches the transparent substrate 7 through the adhesive layer 6. Further, while the refraction index of air is approximately 1, since the refraction index of the first substrate 51 or the transparent substrate 7 is about 1.5 and the refraction index of the adhesive layer 6 is 1.3 or more and 1.7 or less, the difference between the refraction index of the first substrate 51 or the transparent substrate 7 and the refraction index of the adhesive layer 6 is smaller than the difference between the refraction index of the first substrate 51 or the transparent substrate 7 and the refraction index of air. Thus, loss of the incident light becomes small in a case where the incident light passes through the adhesive layer 6. Accordingly, in the present embodiment, it is possible to reduce loss of the incident light due to reflection.

Second Embodiment

Next, a second embodiment of the invention will be described with reference to the accompanying drawings.

Figure 5:
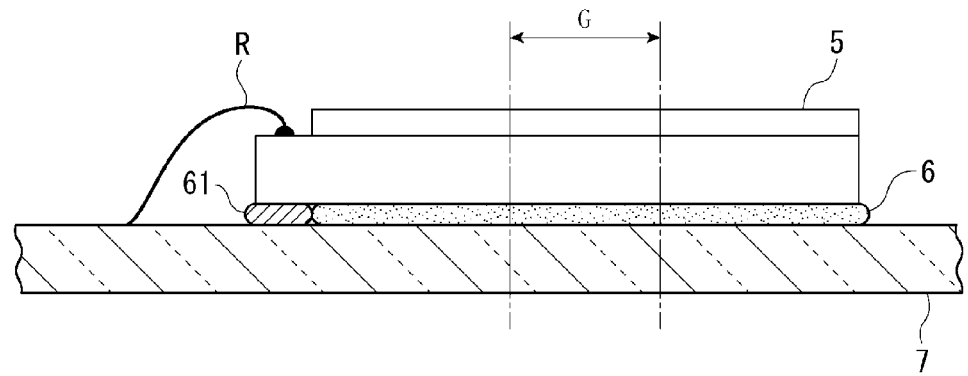
FIG. 5 is a cross-sectional view illustrating the vicinity of an interference filter in an optical module according to a second embodiment.

FIG. 5 is a cross-sectional view illustrating the vicinity of an interference filter 5 in a colorimetry sensor 3 (optical module) according to a second embodiment. Hereinafter, the same reference numerals are given to the same components as in the first embodiment, and its description will be omitted or simplified.

In the colorimetry sensor 3, as shown in FIG. 5, a part of the interference filter 5 is fixed to the transparent substrate 7 through a cured adhesive layer 61 obtained by curing a curable adhesive agent, and the other part of the interference filter 5 is fixed to the transparent substrate 7 through the adhesive layer 6. Further, the interference filter 5 is connected to the voltage control portion 32 by the wiring R. Further, as shown in FIG. 5, the cured adhesive layer 61 is disposed in apart (one location) of a region which overlaps with a first electrode terminal 541B or a second electrode terminal 542B when seen from a plan view.

As the curable adhesive agent for forming the cured adhesive layer 61, a known curable adhesive agent may be normally used. Further, the Young's modulus of the cured adhesive layer 61 is 1 MPa or more.

Effects in the Second Embodiment

In the colorimetry sensor 3 according to the present embodiment, the part of the interference filter 5 is fixed to the transparent substrate 7 through the cured adhesive layer 61. In a case where the curable adhesive agent is used, it is possible to reliably fix the interference filter 5 to the transparent substrate 7, compared with a case where the gel-like resin is used. Further, it is possible to suppress the position deviation of the interference filter 5. On the other hand, in the other part of the interference filter 5, since the interference filter 5 is fixed to the transparent substrate 7 through the adhesive layer 6, in a similar way to the first embodiment, it is possible to sufficiently suppress occurrence of the distortion in the interference filter 5. In this way, it is possible to enhance the adhesive strength between the interference 5 and the transparent substrate 7.

Further, in the colorimetry sensor 3 according to the present embodiment, the Young's modulus of the cured adhesive layer 61 is 1 MPa or more. In such a case, it is possible to reliably fix the interference filter 5 on the transparent substrate 7, compared with the case where the gel-like resin is used. Thus, in this embodiment, it is possible to enhance the adhesive strength between the interference filter 5 and the transparent filter 7.

Further, in the colorimetry sensor 3 according to the present embodiment, the cured adhesive layer 61 is disposed in a part of the region which overlaps with the first electrode terminal 541B or the second electrode terminal 542B when seen from a plan view. In the portion of the interference filter 5 where the first electrode terminal 541B or the second electrode terminal 542B is disposed, even though the distortion occurs, the distortion does not significantly affect the spectral accuracy of the interference filter 5. In this way, it is possible to enhance the adhesive strength between the interference filter 5 and the transparent substrate 7 while sufficiently maintaining the spectral accuracy. Further, even though outer stress is applied when the wiring is disposed in the first electrode terminal 541B or the second electrode terminal 542B, it is possible to suppress a problem such as position distortion or inclination of the interference filter 5, for example.

Third Embodiment

Next, a third embodiment of the invention will be described with reference to the accompanying drawings.

Figure 6:
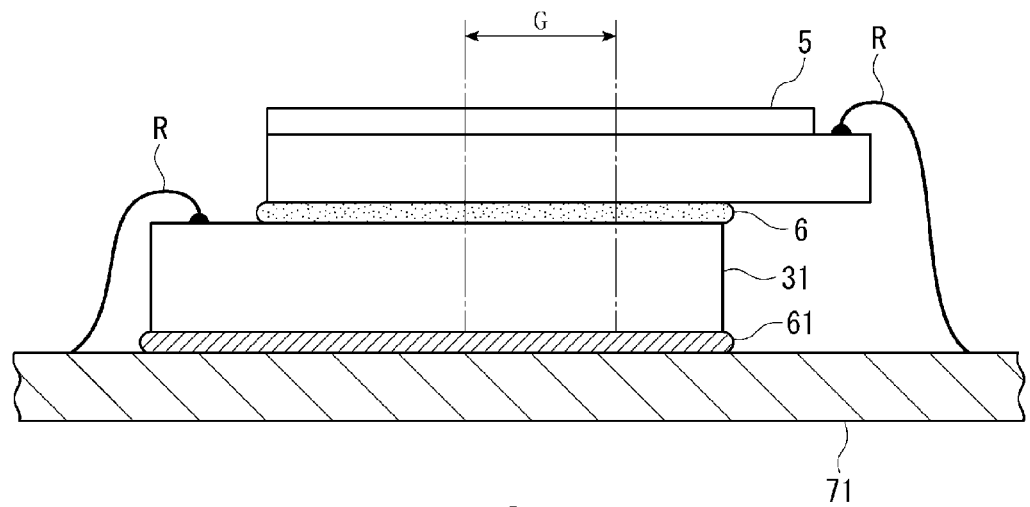
FIG. 6 is a cross-sectional view illustrating the vicinity of an interference filter in an optical module according to a third embodiment.

FIG. 6 is a cross-sectional view illustrating the vicinity of an interference filter 5 in a colorimetry sensor 3 (optical module) according to a third embodiment.

In the colorimetry sensor 3, as shown in FIG. 6, the interference filter 5 is fixed to the light receiving device 31 through the adhesive layer 6, and the light receiving device 31 is fixed to a support substrate 71 through the cured adhesive layer 61. Further, the interference filter 5 is connected to the voltage control portion 32 by the wiring R. The light receiving device 31 is connected to the colorimetry processing portion 43 by the wiring R. Further, the adhesive layer 6 is disposed in the light transmission region G and a region which overlaps with the light receiving device 31 when seen from a plan view.

Here, as the support substrate 71, the transparent substrate 7 may be used, but since the incident light incident on the interference filter 5 does not reach the support substrate 71, a substrate which does not transmit light of the visible light range may be used.

Effects in the Third Embodiment

In the colorimetry sensor 3 according to the present embodiment, since the interference filter 5 is fixed to the light receiving device 31 through the adhesive layer 6, it is possible to use the colorimetry sensor 3 as a desirable optical module as it is.

Fourth Embodiment

Next, a fourth embodiment of the invention will be described with reference to the accompanying drawings.

Figure 7:
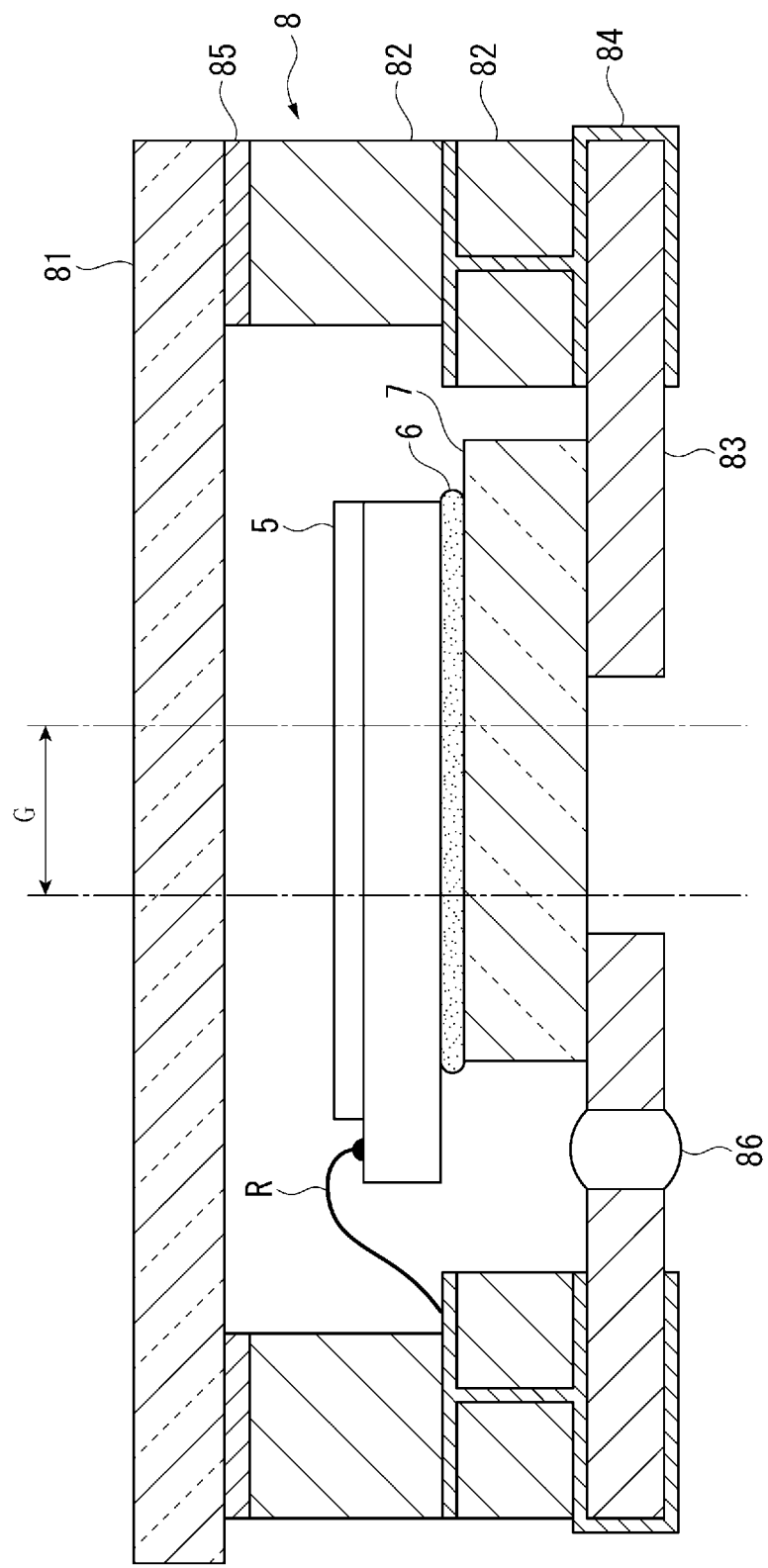
FIG. 7 is a cross-sectional view illustrating the vicinity of an interference filter in an optical module according to a fourth embodiment.

FIG. 7 is a cross-sectional view illustrating the vicinity of an interference filter 5 in a colorimetry sensor 3 (optical module) according to the fourth embodiment.

The colorimetry sensor 3 includes the interference filter 5 and the transparent substrate 7, as shown in FIG. 7, and also includes a casing 8 which accommodates the interference filter 5 and the transparent substrate 7. In the colorimetry sensor 3, the interference filter 5 is fixed to the transparent substrate 7 through the adhesive layer 6, which are accommodated in the casing 8.

As shown in FIG. 7, the casing 8 includes a transparent upper surface portion 81 which covers an upper front surface side of the interference filter 5 and is made of a material capable of transmitting light of the visible light range, a side surface portion 82 which covers side surfaces of the interference filter 5 and the transparent substrate 7, and a lower surface portion 83 which supports a part of the lower front surface side of the transparent substrate 7. The side surface portion 82 is bonded by a conductive member 84 such as a conductive paste, which is bonded with the lower surface portion 83 by the conductive member 84. Further, the side surface portion 82 is bonded with the transparent upper surface portion 81 by a bonding member 85 such as glass paste. The lower surface portion 83 has two large and small through holes, in which the large through hole is blocked with the transparent substrate 7 and the small through hole is blocked with a sealing member 86 such as a metallic ball.

Further, the interference filter 5 is connected to the voltage control portion 32 through the conductive member 84 by the wiring R.

In the casing 8, the transparent upper surface portion 81 can make the light incident on the light transmission region G of the interference filter 5, and the transparent upper surface portion 81 serves as a light incident window (optical incident substrate). Further, as shown in FIG. 7, in a portion of the lower surface portion 83 which does not support the transparent substrate 7, the light passed through the light transmission region G of the interference filter 5 can exit, and this portion serves as a light exiting window (optical exiting substrate).

Effects in the Fourth Embodiment

In the colorimetry sensor 3 according to the present embodiment, the interference filter 5 is accommodated in the casing 8. Thus, by filling an inert gas in the casing 8 or by decompressing the casing 8, it is possible to suppress deterioration due to oxidation or the like of the interference filter 5.

Further, the casing 8 may be hermetic to be in a vacuum state, and in this case, when the movable portion 521 in the interference filter 5 is displaced, it is possible to reduce drive power when the movable portion 521 is driven without air resistance, thereby achieving power saving.

Further, in the colorimetry sensor 3 according to the present embodiment, since the casing 8 includes the light incident window and the light exiting window, if the light receiving device 31 is disposed so that the light passed through the casing 8 is incident on the light receiving device 31, it is possible to use the colorimetry sensor as a desirable optical module.

Other Embodiments

The invention is not limited to the above-described embodiments, and modifications and improvements are possible in a range without departing from the spirit of the invention.

For example, in the above-described embodiments, the interference filter 5 is fixed to the transparent substrate 7 or the light receiving device 31, but the fixing portion for fixing the interference filter 5 is not limited thereto. As the fixing portion, any member which forms the colorimeter 1 may be used.

Figure 8:
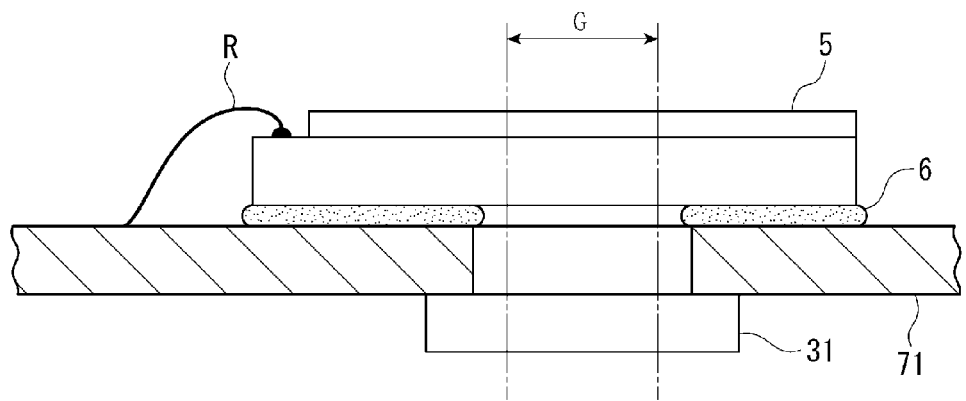
FIG. 8 is a cross-sectional view illustrating the vicinity of an interference filter in an optical module according to another embodiment of the invention.

Further, the fixing portion may be a member which does not transmit light of the visible light range. In such a case, for example, as shown in FIG. 8, the interference filter 5 may be fixed to the support substrate 71 having a through hole through the adhesive layer 6, and the light passed through the light transmission region G of the interference filter 5 may be incident on the light receiving device 31. With such a configuration, it is possible to use the colorimetry sensor as a desirable optical module as it is.

In the above-described embodiment, the interference filter 5 is connected to the voltage control portion 32 by the wiring R, but a print wiring substrate having flexibility instead of the wiring R may be used.

Further, in the above-described embodiment, a mirror fixing surface of the mirror fixing portion 512 which faces the second substrate 52 is formed close to the second substrate 52 compared with an electrode fixing surface, but the invention is not limited thereto. The height positions of the electrode fixing surface and the mirror fixing surface are appropriately set by the size of a gap between the first reflection film 56 fixed on the mirror fixing surface and the second reflection film 57 formed on the second substrate 52, the interval between the first electrode 541 and the second electrode 542, the thickness of the first reflection film 56 or the second reflection film 57, and the like. Accordingly, for example, a configuration in which the electrode fixing surface and the mirror fixing surface are formed on the same surface, a configuration in which a cylindrical groove shaped mirror fixing groove is formed in a central portion of the electrode fixing surface and the mirror fixing surface is formed on the bottom of the mirror fixing groove, or similar configurations may be used.

Further, in a case where the gap (inter-electrode gap) between the electrodes 541 and 542 is larger than the gap (inter-mirror gap) between the reflection films 56 and 57, it is necessary to apply a large drive voltage for changing the inter-mirror gap. On the other hand, as described above, in a case where the inter-mirror gap is larger than the inter-electrode gap, it is possible to lessen the drive voltage for changing the inter-mirror gap, thereby achieving power saving. Further, since the interference filter having such a configuration has a large inter-mirror gap, it is particularly effective to measure spectral characteristics in a long wavelength region. For example, the interference filter may be mounted to a module for realizing infrared light analysis used for the above-described gas analysis or the like or optical communication.

Further, the diaphragm-shaped holding portion 522 is disposed on the second substrate 52 of the interference filter 5, but for example, a plurality of beam-shaped holding portions disposed in positions which are point-symmetric to the center of the movable portion 521 may be disposed.

In the above-described embodiment, the colorimetry sensor 3 is provided as the optical module according to the invention and the colorimeter 1 having the colorimetry sensor 3 is provided as the electronic apparatus, but the invention is not limited thereto. For example, a gas sensor which receives inflow of gas therein and detects light absorbed by the gas in the incident light may be used as the optical module according to the invention, and a gas detection apparatus which analyzes and determines the gas flowed into the sensor by the gas sensor may be used as the electronic apparatus according to the invention. Further, the electronic apparatus may be a spectral camera or a spectral analysis apparatus having the above-described optical module. Further, by changing the intensity of the light of each wavelength over time, it is possible to transmit data by the light of each wavelength. In this case, by separating light of a specific wavelength by the interference filter 5 disposed in the optical module and receiving the light by a light receiving portion, it is possible to extract data transmitted by the light of the specific wavelength. Thus, by processing the data of the light of each wavelength by the electronic apparatus including such a data extraction optical module, it is possible to perform optical communication.

The colorimeter 1 is provided as the electronic apparatus according to the invention, but the optical module and the electronic apparatus of the invention may be used in a variety of fields.

For example, it is possible to use the optical module and the electronic apparatus as a light-based system for detecting the presence of a specific substance. As such a system, for example, a gas detection apparatus such as a vehicle gas leakage detector for detecting a specific gas with high sensitivity by a spectral colorimetry method using the interference filter according to the invention or an optoacoustic rare gas detector for a breath test may be used.

An example of such a gas detection apparatus will be described with reference to the drawings.

Figure 9:
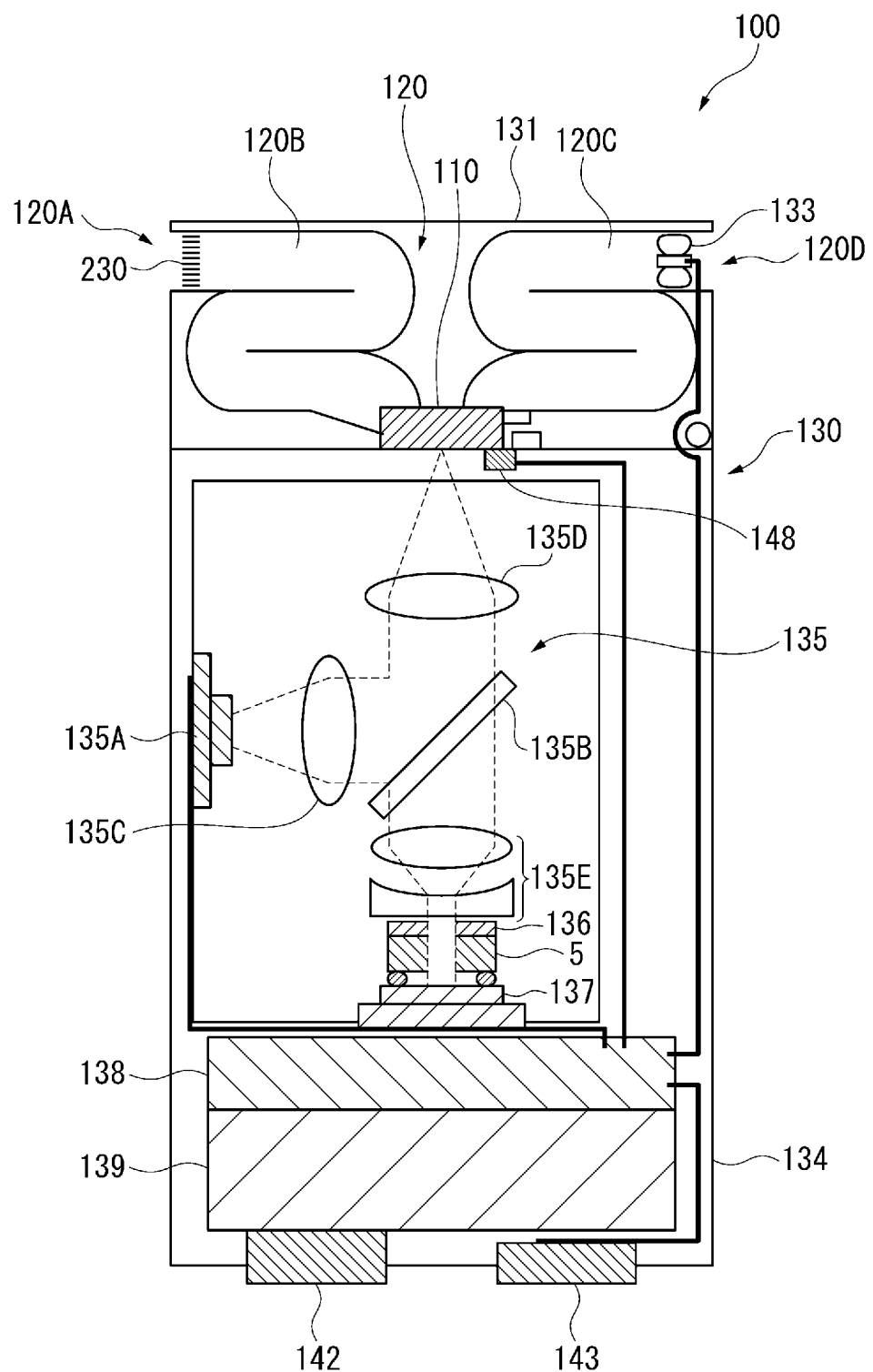
FIG. 9 is a diagram schematically illustrating a configuration of a gas detection apparatus which is an example of an electronic apparatus according to another embodiment of the invention.

FIG. 9 is a diagram schematically illustrating an example of the gas detection apparatus including the interference filter.

Figure 10:
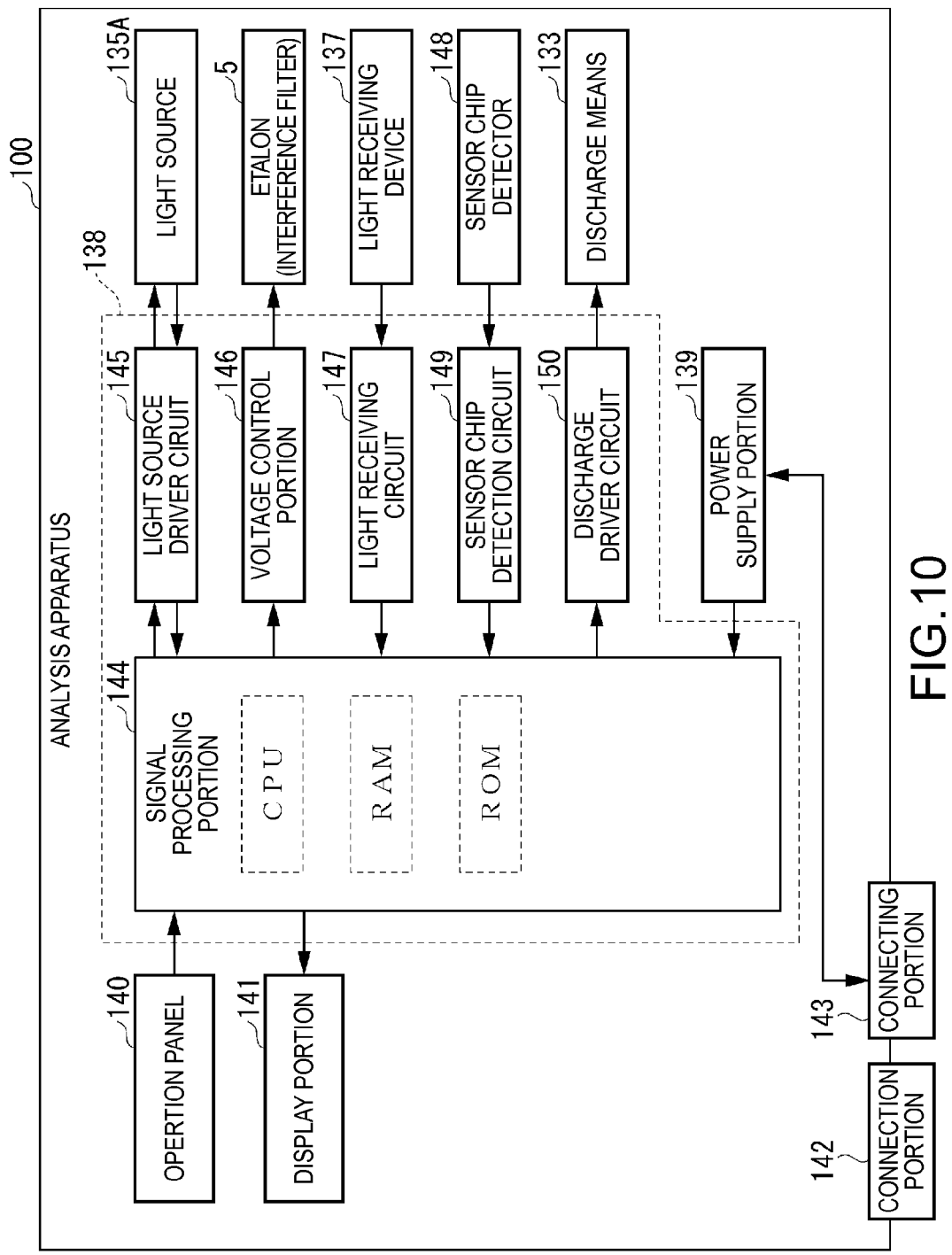
FIG. 10 is a block diagram illustrating a configuration of a control system of a gas detection apparatus in FIG. 9.

FIG. 10 is a block diagram illustrating a configuration of a control system of the gas detection apparatus in FIG. 9.

As shown in FIG. 9, a gas detection apparatus 100 includes a sensor chip 110, a flow path 120 which has an absorption port 120A, an absorption flow path 120B, a discharge flow path 120C and a discharge port 120D, and a main body portion 130.

The main body portion 130 includes a detecting portion (optical module) which includes a sensor portion cover 131 having an opening capable of opening and closing the flow path 120, a discharge unit 133, a casing 134, an optical portion 135, a filter 136, an interference filter 5, a light receiving device 137 (light receiving portion) and the like, a control portion 138 which processes a detected signal and controls the detecting portion, a power supply portion 139 which supplies electric power, and the like. Further, the optical portion 135 includes a light source 135A which emits light, a beam splitter 135B which reflects the light incident from the light source 135A to the sensor chip 110 and transmits the light incident from the sensor chip to the light receiving device 137, and lenses 135C, 135D and 135E.

Further, as shown in FIG. 10, on a front surface of the gas detection apparatus 100, an operation panel 140, a display portion 141, a connection portion 142 for interface with the outside, and the power supply portion 139 are provided. In a case where the power supply portion 139 is a secondary battery, the gas detection apparatus 100 may include a connection portion 143 for charging.

Further, as shown in FIG. 10, the control portion 138 of the gas detection apparatus 100 includes a signal processing portion 144 which is configured by a CPU or the like, a light source driver circuit 145 for controlling the light source 135A, a voltage control portion 146 for controlling the interference filter 5, a light receiving circuit 147 which receives a signal from the light receiving device 137, a sensor chip detection circuit 149 which reads a code of the sensor chip 110 and receives a signal from a sensor chip detector 148 which detects the presence or absence of the sensor chip 110, a discharge driver circuit 150 which controls the discharge unit 133, and the like.

Hereinafter, an operation of the above-described gas detection apparatus 100 will be described.

The sensor chip detector 148 is disposed in the sensor portion cover 131 above the main body portion 130, and the sensor chip detector 148 detects the presence or absence of the sensor chip 110. If the detection signal from the sensor chip detector 148 is detected, the signal processing section 144 determines that the sensor chip 110 is installed and outputs a display signal indicating that a detection operation can be performed to the display portion 141.

Further, for example, if the operation panel 140 is operated by a user and a signal indicating that the detection process is started from the operation panel 140 is output to the signal processing portion 144, firstly, the signal processing section 144 outputs a light source operating signal to the light source driver circuit 145 to operate the light source 135A. If the light source 135A is driven, laser light having stable linear polarization with a single wavelength is emitted from the light source 135A. Further, a temperature sensor or a light quantity sensor is installed in the light source 135A, and information thereof is output to the signal processing portion 144. Further, if it is determined that the light source 135A is stably operated on the basis of the temperature or light quantity input from the light source 135A, the signal processing section 144 controls the discharge driver circuit 150 to operate the discharge unit 133. Thus, the gas sample including a target substance (gas molecule) to be detected is introduced to the absorption flow path 120B, the inside of the sensor chip 110, the discharge flow path 120C and the discharge port 120D from the absorption port 120A.

Further, the sensor chip 110 is a sensor which includes a plurality of metal nanostructures therein and uses localized surface plasmon resonance. In such a sensor chip 110, a strong electric field is formed between the metal nanostructures by the laser light. Further, if the gas molecule comes into the strong electric field, Raman scattering light including information about molecule vibration or Rayleigh scattering light are generated.

The Rayleigh scattering light or the Raman scattering light is incident on the filter 136 through the optical portion 135, and the Rayleigh scattering light is separated by the filter 136 and the Raman scattering light is incident on the interference filter 5. Further, the signal processing portion 144 controls the voltage control portion 146 to adjust voltage applied to the interference filter 5, to thereby separate the Raman scattering light corresponding to the gas molecule which is the detection target by the interference filter 5. Thereafter, if the light receiving portion 137 receives the separated light, a light receiving signal according to the amount of received light is output to the signal processing portion 144 through the light receiving circuit 147.

The signal processing portion 144 compares spectral data on the Raman scattering light corresponding to the gas molecule which is the detection target obtained as described above with data stored in a ROM, determines whether the gas molecule is a desired gas molecule and specifies the substance. Further, the signal processing portion 144 displays result information to the display portion 141 or outputs the result information outside the connecting portion 142.

In FIGS. 9 and 10, the gas detection apparatus 100 which separates the Raman scattering light by the interference filter 5 and performs gas detection from the separated Raman scattering light is provided as an example, but the gas detection apparatus may be used as a gas detection apparatus which specifies the gas type by detecting the light absorption level specific to the gas. In this case, a gas sensor which receives inflow of gas therein and detects the absorbed light by the gas among the incident light is used as the optical module according to the invention. Further, a gas detection apparatus which analyzes and determines the gas flowed in the gas sensor by this gas sensor is used as the electronic apparatus according to the invention. In such a configuration, it is possible to detect the component of the gas using the interference filter according to the invention.

Further, the system for detecting the presence of the specific substance is not limited to the above-described gas detection, but may be configured by a substance component analysis apparatus such as a non-invasive measurement apparatus of saccharides using a near infrared light spectrum or a non-invasive measurement apparatus of information about plants, living bodies, minerals or the like.

Figure 11:
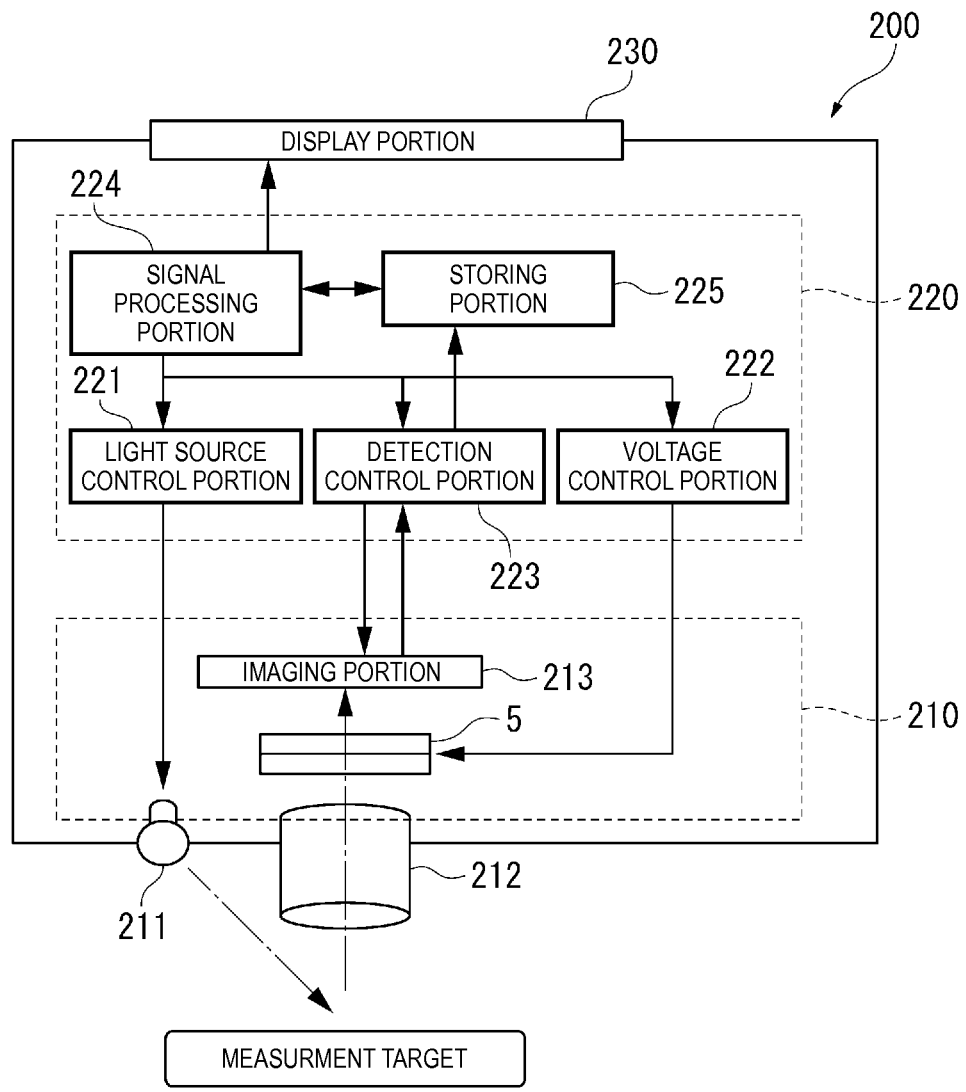
FIG. 11 is a diagram schematically illustrating a configuration of a plant analysis apparatus which is an example of an electronic apparatus according to another embodiment of the invention.

Hereinafter, as an example of the substance component analysis apparatus, a plant analysis apparatus will be described. FIG. 11 is a diagram schematically illustrating a plant analysis apparatus which is an example of the electronic apparatus using the interference filter 5.

As shown in FIG. 11, a plant analysis apparatus 200 includes a detector 210 (optical module), a control portion 220, and a display portion 230. The detector 210 includes a light source 211 which exits light, an imaging lens 212 through which light is introduced from a measurement target, an interference filter 5 which separates the light introduced through the imaging lens 212, and an imaging portion 213 which detects the separated light (light receiving portion).

Further, the control portion 220 includes a light source control portion 221 which performs a lighting-up and lighting-out control of the light source 211 and a brightness control at the time of lighting-up, a voltage control portion 222 which controls the interference filter 5, a detection control portion 223 which controls the imaging portion 213 to obtain a spectral image which is captured by the imaging device 213, a signal processing portion 224, and a storing portion 225.

If the system of the plant analysis apparatus 200 is driven, the light source 211 is controlled by the light source control portion 221, so that light is emitted to the measurement target from light source 211. Further, the light reflected from the measurement target is incident on the interference filter 5 through the imaging lens 212. The interference filter 5 is supplied with voltage capable of separating a desired wavelength under the control of the voltage control portion 222, and the separated light is captured by the imaging portion 213 formed by a CCD camera or the like, for example. Further, the captured image is stored in the storing portion 225 as the spectral image. Further, the signal processing portion 224 controls the voltage control portion 222 to change a voltage value applied to the interference filter 5, and obtains the spectral image for each wavelength.

Further, the signal processing portion 224 performs a calculation process for data on each pixel in each image stored in the storing portion 225, and calculates a spectrum in each pixel. Further, for example, information relating to the component of the plant corresponding to the spectrum is stored in the storing portion 225, and the signal processing portion 224 analyzes the calculated data about the spectrum on the basis of the information relating to the plant stored in the storing portion 225, and calculates the plant component included in the detection target and its content. Further, it is possible to calculate plant calorie or freshness from the obtained plant component and its content. Further, by analyzing spectrum distribution in the image, for example, it is possible to perform extraction of a portion where the freshness is reduced in the plant which is the inspection target, and to perform detection of foreign substances included in the plant.

Further, the signal processing portion 224 performs a process of displaying information about the component, content, calorie, freshness or the like of the plant which is the inspection target obtained as described above on the display portion 230.

Further, in FIG. 11, the plant analysis apparatus 200 is described as an example, but the invention may be applied to the non-invasive measurement apparatus of the above mentioned different information having approximately the same configuration. For example, the invention may be applied to a bioanalysis apparatus which analyzes living body components, such as measurement and analysis of a liquid component such as blood. As such a bioanalysis apparatus, for example, if an apparatus of detecting ethyl alcohol is used as the apparatus of measuring the liquid component such as blood, it is possible to use the apparatus as a drunken driving prevention apparatus which detects a drunken state of a driver. Further, it is possible to provide an electronic endoscope system including such a bioanalysis apparatus.

Further, the invention may be applied to a mineral analysis apparatus which performs a mineral component analysis.

Further, the optical module and the electronic apparatus of the invention may be applied to the following apparatuses.

For example, by changing the intensity of light of each wavelength over time, it is possible to transmit data by the light of each wavelength. In this case, by separating light of a specific wavelength by the interference filter disposed in the optical module and receiving the separated light by a light receiving portion, it is possible to extract data transmitted by the light of the specific wavelength. Thus, by processing the data of the light of each wavelength by the electronic apparatus including such a data extraction optical module, it is possible to perform optical communication.

Further, the electronic apparatus may be applied to a spectral camera, a spectral analyzer, or the like which captures a spectral image by separating the light by the interference filter according to the invention. As an example of such a spectral camera, an infrared light camera in which the interference filter is built-in is used.

Figure 12:
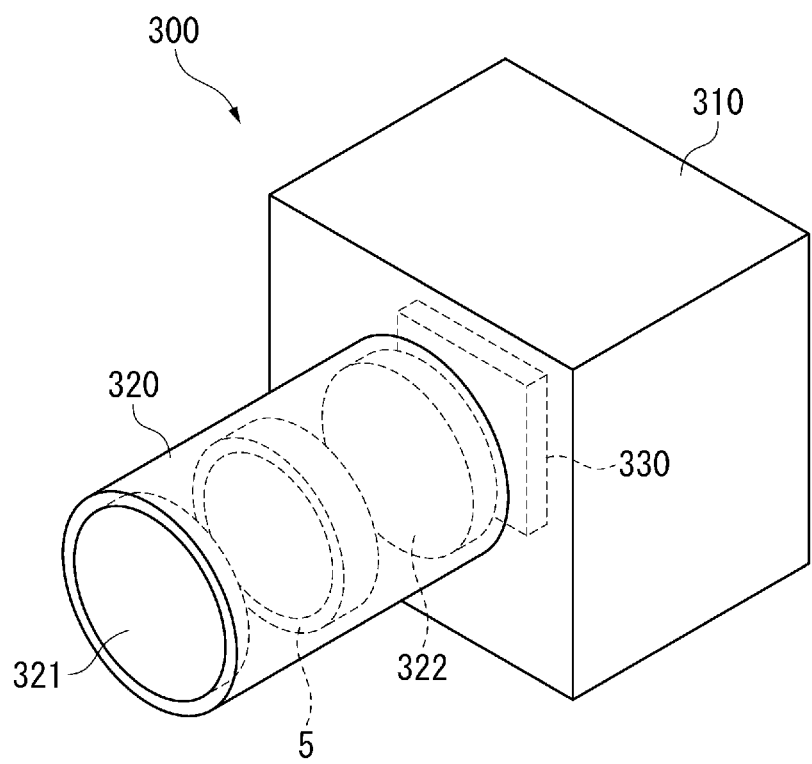
FIG. 12 is a diagram schematically illustrating a spectral camera which is an example of an electronic apparatus according to another embodiment of the invention.

FIG. 12 is a diagram schematically illustrating a configuration of a spectral camera. As shown in FIG. 12, a spectral camera 300 includes a camera main body 310, an imaging lens unit 320, and an imaging portion 330.

The camera main body 310 is a portion which is gripped by a user for operation.

The imaging lens unit 320 is installed in the camera main body 310, and guides incident image light to the imaging portion 320. Further, as shown in FIG. 12, the imaging lens unit 320 includes an objective lens 321, an image forming lens 322, and an interference filter 5 which is disposed between these lenses. The imaging portion 330 is configured by a light receiving device, and captures the image light guided by the imaging lens unit 320. In such a spectral camera 300, by transmitting the light of wavelength which is an imaging target by the interference filter 5, it is possible to capture the spectral image of the light of a desired wavelength.

Further, the interference filter according to the invention may be used as a bandpass filter, and for example, may be used as an optical laser apparatus which separates and transmits only light in a narrow band centering around a predetermined wavelength among light of a predetermined wavelength range which is emitted from the light emitting device, by the interference filter.

Further, the interference filter according to the invention may be used as a biometric authentication apparatus, and for example, may be applied to an authentication apparatus of blood vessel, fingerprint, retina, iris or the like, which uses light in a near infrared light range or a visible range.

Further, the optical module and the electronic apparatus may be used as a concentration detection apparatus. In this case, the concentration detection apparatus separates and analyzes infrared energy (infrared light) emitted from a substance by the interference filter, and measures the concentration of an object to be inspected in a sample.

As described above, the optical module and the electronic apparatus according to the invention may be applied to any apparatus which separates predetermined light from incident light. Further, as described above, since the interference filter according to the invention can separate a plurality of wavelengths by one device, it is possible to perform measurement of a spectrum of the plurality of wavelengths and detection of a plurality of components with high accuracy. Accordingly, it is possible to achieve a small-sized optical module or electronic apparatus compared with the apparatus in the related art which extracts a desired wavelength by a plurality of devices, and for example, it is possible to preferably use the optical module or electronic apparatus according to the invention as a mobile or vehicle optical device.

Further, specific structures and procedures in the embodiments of the invention may be appropriately changed to other structures and the like in a range without departing from the spirit of the invention.

What is claimed is:

1. An optical module comprising:
an interference filter including a first substrate having a first thermal expansion coefficient, a second substrate which faces the first substrate, a first reflection film which is formed on the first substrate, and a second reflection film which is formed on the second substrate and faces the first reflection film through a gap; and
a fixing portion to which the first substrate of the interference filter is fixed, having a second thermal expansion coefficient which has a value different from the first thermal expansion coefficient,
wherein the interference filter is fixed to the fixing portion by way of a first adhesive layer that is located outside of a transmission region of the interference filter, the first adhesive layer being formed on a surface of the first substrate that is opposite to a surface of a first reflection film side of the first substrate,
a part of the interference filter is fixed to the fixing portion by way of a second adhesive layer that does not overlap the first adhesive layer, and
a Young's modulus of the first adhesive layer is less than a Young's modulus of the second adhesive layer.

2. The optical module according to claim 1,
wherein the Young's modulus of the first adhesive layer is 10 kPa or more and 100 kPa or less, and
wherein the Young's modulus of the second adhesive layer is 1 MPa or more.

3. The optical module according to claim 1,
wherein the second adhesive layer is disposed along only one part of the interference filter.

4. The optical module according to claim 1,
wherein when a thickness of the first adhesive layer is Ta (mm), a linear expansion coefficient of the first substrate is $\alpha1$ (K$^{-1}$), a Young's modulus of the first substrate is E1 (GPa), a thickness of the first substrate is T1 (mm), a linear expansion coefficient of the fixing portion is $\alpha2$ (K$^{-1}$), a Young's modulus of the fixing portion is E2 (GPa), a thickness of the fixing portion is T2 (mm), and a coefficient based on a material of the first adhesive layer is A, the thickness of the first adhesive layer satisfies the following formula (1) in a case where $(\alpha1 \cdot E1 \cdot T1^2) \leq (\alpha2 \cdot E2 \cdot T2^2)$, and satisfies the following formula (2) in a case where $(\alpha1 \cdot E1 \cdot T1^2) > (\alpha2 \cdot E2 \cdot T2^2)$:

$$Ta \geq A \cdot (\alpha2 \cdot E2 \cdot T2^2)/(\alpha1 \cdot E1 \cdot T1^2) \qquad (1)$$

$$Ta \geq A \cdot (\alpha1 \cdot E1 \cdot T1^2)/(\alpha2 \cdot E2 \cdot T2^2) \qquad (2).$$

5. The optical module according to claim 1,
wherein the first substrate and the second substrate are glass substrates.

6. The optical module according to claim 1,
wherein the interference filter includes an electrode terminal which is disposed on the first substrate, and
wherein the second adhesive layer is disposed in a part of a region which overlaps with the electrode terminal from a plan view when the first substrate and the second substrate are seen in a substrate thickness direction.

7. The optical module according to claim 1,
wherein the fixing portion is a light receiving element which receives light which passes through the interference filter.

8. The optical module according to claim 1, further comprising:
a casing which includes an exterior portion, a light incident substrate through which light incident on the interference filter is introduced and a light exiting substrate through which light passing through the interference filter exits, and is formed therein with a hermetically sealed space,
wherein the interference filter is accommodated in the casing.

9. The optical module according to claim 8,
wherein the fixing portion is the light exiting substrate of the casing.

10. An electronic apparatus comprising the optical module according to claim 1.

* * * * *